United States Patent [19]

Ecke, Jr.

[11] Patent Number: Plant 6,694

[45] Date of Patent: Mar. 28, 1989

[54] POINSETTIA PLANT NAMED LILO

[76] Inventor: Paul Ecke, Jr., 441 Saxony Rd., Encinitas, Calif. 92024

[21] Appl. No.: 75,056

[22] Filed: Jul. 17, 1987

[51] Int. Cl.[4] ..... A01H 5/00
[52] U.S. Cl. ..... Plt./86
[58] Field of Search ..... Plt./86

*Primary Examiner*—Robert E. Bagwill
*Attorney, Agent, or Firm*—Charles W. Rummler

[57] ABSTRACT

A new Poinsettia cultivar, distinguished by intense dark red bracts and intense dark green foliage with self-branching characteristics, is described herein. The new plant produces a very desirable pinched, branched flowering potted plant. Equally desirable, the new plant is resistant to become epinastic after being confined to shipping containers, and recovers rapidly if the plant does become epinastic. The post-production foliage and bract retention is excellent even under low light intensities in the consumer's home.

1 Drawing Sheet

BACKGROUND OF THE NEW PLANT

This new Poinsettia originated as a seedling produced by crossing seedling parents of unknown origin. I selected this new Poinsettia from among many seedlings which resulted from the breeding program being conducted in my greenhouses in Encinitas, Calif., and I was attracted to this seedling because of several desirable traits. Particularly because the color of the bracts is an intense dark red and the foliage is an intense dark green. The plant is also unique in two aspects. Unlike other poinsettias with intense dark coloration, this new variety is self-branching and produces a very desirable pinched plant. Equally desirable, the plant is resistant to becoming epinastic after being confined in shipping containers during the marketing process. I propagated this plant by cuttings through successive generations and find it has retained all of these desirable traits from generation to generation and they appear to be firmly fixed.

DESCRIPTION OF THE DRAWINGS

My new variety of Poinsettia is illustrated by the accompanying photographic drawings sheet one of which has two views in full color the upper one of which shows a full face view of the flower clusters and surrounding bracts and the lower view shows a typical potted plant in full bloom, sheet two is an enlarged print of the upper view of sheet one, which has been hand painted to show the true bract colors; the color rendition in both views of sheet one being as close to that herein specified as is reasonably possible to obtain by conventional photographic procedures.

DESCRIPTION OF THE NEW PLANT

Figure 1:
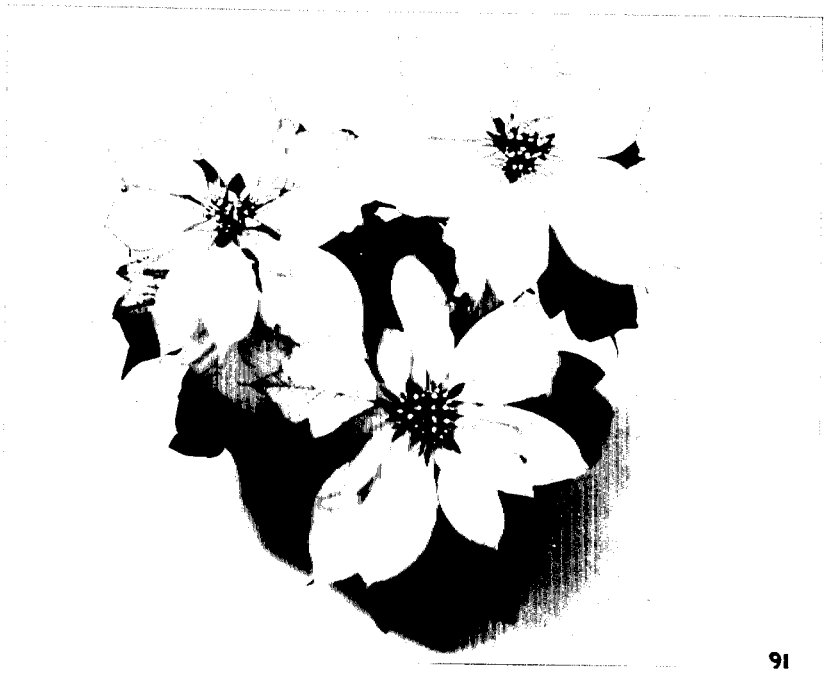
Figure 2:
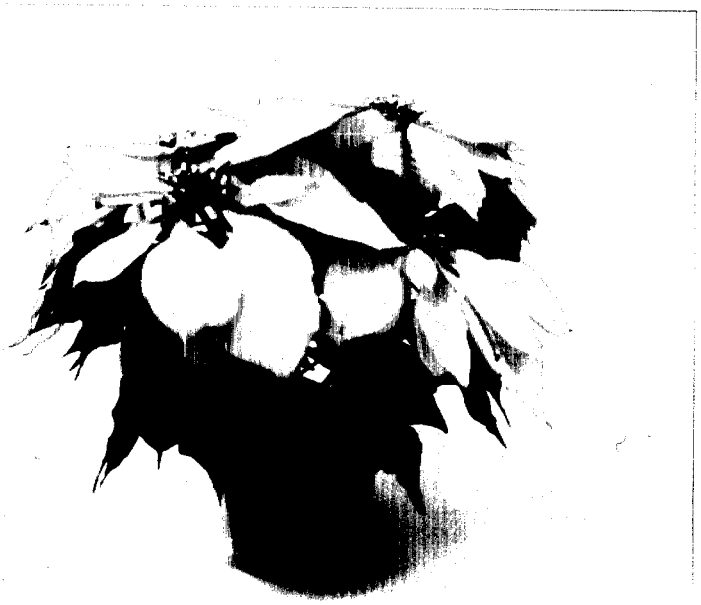
Figure 1:
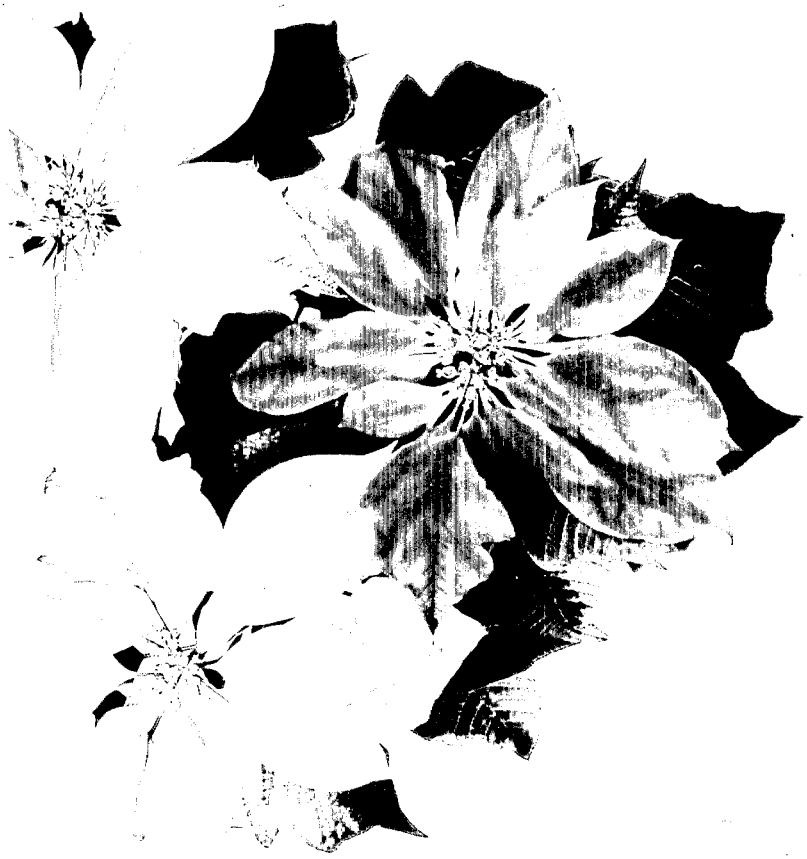

The following is a detailed description of this new Poinsettia variety as observed in my greenhouse at Encinitas, Calif., during December 1986, with color designations according to The R.H.S. Colour Chart published in 1966 by The Royal Horticultural Society at London, England.

THE PLANT

Origin: Seedling.
Classification:
*Botanic.—Euphorbia pulcherrima.*
Form: Shrub.
Height: Medium.
Growth habit: As a single stem, upright and vigorous with many self-branching side shoots. May require a growth regulator. I have observed single stem plants with an average height of about 45–50 cm. and an overall bract presentation diameter of about 35 cm.
Branching: Upright with many stems producing a bushy, full appearance. Pinched plants with five branches and an overall height of 35–40 cm. had flowers with an overall bract presentation diameter of about 25–30 cm.
Growth rate: Very fast. Rooting occurs in 12–18 days under intermittent mist. The plant will bloom in about nine weeks under continuous long night conditions and night temperatures of about 16–18 degrees C. during October and November. Flowering may be somewhat delayed and bract color not as intense at higher temperatures.
Foliage: The foliage is clean and uniformly dark green from bottom to top of the plant. The leaves are of medium size, leaf blades typically being about 10–14 cm. long and about 8–10 cm. wide with leaf petioles about 5–7 cm. long.
Leaf shape: Typical leaves vary from ovate with entire leaf margins to broad ovate with weakly developed lobes.
Color:
*Upper side.*—Darker than RHS 131A
*Under side.*—Near RHS 139A.
Retention: The foliage lasts extremely well even under low light intensities in the consumer's home. Leaf retention is better than the Poinsettia 'Annette Hegg Dark Red' (U.S. Plant Pat. No. 3,160).
Bracts: Generally there are 18–21 uniformly colored bracts of various sizes subtending the cyathia. The primary bracts have blades typically 12–15 cm. long and 7–9 cm. wide with petioles about 2–4 cm. long.
Shape: Ovate to elliptic to obovate, with mostly entire leaf margins, but occasionally weakly lobed.
Color:
*Upper side.*—Darker than RHS 46B, near RHS 46A.
*Under side.*—Darker than RHS 45D, near RHS 45C.

I claim:

1. The new and distinctive Poinsettia cultivar and parts thereof, substantially as herein shown and described, distinguished by intense dark red bracts and intense dark green leaves, a self-branching habit, its resistance to epinasty during post-production handling, and its extraordinary ability to retain its foliage in the consumer's home.

* * * * *